(12) United States Patent
Blanco

(10) Patent No.: US 11,867,633 B2
(45) Date of Patent: Jan. 9, 2024

(54) CONTROLLED DOPING OF ANODIC ALUMINUM OXIDE FOR ENHANCED FLUORESCENCE AND METHODS OF PREPARATION

(71) Applicant: Nanopec, Inc., Tucson, AZ (US)

(72) Inventor: Mario Blanco, Tucson, AZ (US)

(73) Assignee: Nanopec, Inc., Tucson, AZ (US)

( * ) Notice: Subject to any disclaimer, the term of this patent is extended or adjusted under 35 U.S.C. 154(b) by 449 days.

(21) Appl. No.: 16/799,169

(22) Filed: Feb. 24, 2020

(65) Prior Publication Data

US 2021/0262939 A1    Aug. 26, 2021

(51) Int. Cl.
*G01N 21/76* (2006.01)
*C09K 11/07* (2006.01)
(Continued)

(52) U.S. Cl.
CPC ............ *G01N 21/76* (2013.01); *B82Y 15/00* (2013.01); *B82Y 20/00* (2013.01); *C09K 11/02* (2013.01);
(Continued)

(58) Field of Classification Search
CPC .. G01N 21/76; G01N 21/6408; G01N 33/553; G01N 2021/6439; G01N 21/645;
(Continued)

(56) References Cited

U.S. PATENT DOCUMENTS

2006/0228813 A1\* 10/2006 Wu ...................... G01N 33/553
428/404

2011/0235766 A1\* 9/2011 Stora ........................ H05H 6/00
376/151
2014/0151234 A1\* 6/2014 Irgum ..................... C25D 11/18
205/112

OTHER PUBLICATIONS

Gaponenko et al., "Room-temperature photoluminescence from porous anodic alumina films with embedded terbium and europium species", Materials Letters, 2009, 63, 621-624 (Year: 2009).\*

(Continued)

*Primary Examiner* — Samuel P Siefke
*Assistant Examiner* — Henry H Nguyen
(74) *Attorney, Agent, or Firm* — David L. Nocilly; Bond, Schoeneck & King PLLC

(57) ABSTRACT

Nano-structured anodic aluminum oxide ceramic films and membranes doped with chelated metals for fluorescence enhancement. Controlled doping during production steps results in the inclusion of traces of ions in the finished materials while maintaining high control over the film structure. This approach yields products suitable for optical applications, including fluorescence enhancement. The nano-structured anodic aluminum oxide ceramic films and membranes are particularly useful for in vitro diagnostics, drug discovery, DNA sequencing, proteomics, immunofluorescence, immunohistochemistry, biosensing, and bio-assay fluorescence technologies such as time resolved Forster resonance energy transfer (TR-FRET), Fluorescence in situ hybridization (FISH), Fluorescence-lifetime imaging microscopy (FLIM), Fluorescence polarization immunoassay (FPIA), Fluorescence anisotropy or fluorescence polarization, Fluorescence recovery after photobleaching (FRAP), Fluorescence Loss in Photobleaching (FLIP), Fluorescence correlation spectroscopy (FCS), and Falck-Hillarp fluorescence (F-H).

12 Claims, 14 Drawing Sheets

(51) Int. Cl.
*C09K 11/02* (2006.01)
*G01N 21/64* (2006.01)
*B82Y 15/00* (2011.01)
*B82Y 20/00* (2011.01)
*G01N 33/553* (2006.01)
*C25D 11/04* (2006.01)
*B01D 71/02* (2006.01)
*B82Y 40/00* (2011.01)

(52) U.S. Cl.
CPC .......... *C09K 11/07* (2013.01); *G01N 21/6408* (2013.01); *G01N 33/553* (2013.01); *B01D 71/025* (2013.01); *B82Y 40/00* (2013.01); *C25D 11/04* (2013.01); *G01N 2021/6439* (2013.01)

(58) Field of Classification Search
CPC ......... B82Y 15/00; B82Y 20/00; B82Y 40/00; C09K 11/02; C09K 11/07; B01D 71/025; C25D 11/04
See application file for complete search history.

(56) References Cited

OTHER PUBLICATIONS

Yamamoto et al., "Coloured materials and photoluminescence centres in anodic film on aluminium", Nature, 1981, 289, 572-574 (Year: 1981).*

Stepniowski et al., "Incorporation of copper chelate ions into anodic alumina walls", 2013, Materials Letters, 106, 242-245 (Year: 2013).*

Stepniowski et al., "Fabrication and Luminescence of Anodic Alumina with Incorporated Vanadyl Citrate Chelate Anions", 2014, J Mater Sci Nanotechnol 1: S102 (Year: 2014).*

Lee et al., "Porous Anodic Aluminum Oxide: Anodization and Templated Synthesis of Functional Nanostructures", Chem. Rev., 2014, 114, 15, 7487-7556 (Year: 2014).*

Velleman et al., "Velleman L, Triani G, Evans PJ, Shapter JG, Losic D. Structural and chemical modification of porous alumina membranes." Microporous and Mesoporous Materials. 2009;126(1-2):87-94 (Year: 2009).*

Cai et al., "A smart membrane with antifouling capability and switchable oil wettability for high-efficiency oil/water emulsions separation", Journal of Membrane Science, 2018, 69-77 (Year: 2018).*

Kim et al., "Easy-to-Fabricate and High-Sensitivity LSPR Type Specific Protein Detection Sensor Using AAO Nano-Pore Size Control", Sensors, 2017, 17(4), 856 (Year: 2017).*

Poinern et al., "Progress in Nano-Engineered Anodic Aluminum Oxide Membrane Development", Materials (Basel), 2011, 4(3):487-526 (Year: 2011).*

Georges, "Lanthanide-sensitized Luminescence and Applications to the Determination of Organic Analytes", Analyst, Dec. 1993, vol. 118 (Year: 1993).*

Binnemans, "Lanthanide-Based Luminescent Hybrid Materials", Chem. Rev., 2009, 109, 9, 4283-4374 (Year: 2009).*

* cited by examiner

CONTROLLED DOPING OF ANODIC ALUMINUM OXIDE FOR ENHANCED FLUORESCENCE AND METHODS OF PREPARATION

BACKGROUND OF THE INVENTION

1. Field of the Invention

The present invention relates to nano-structured anodic aluminum oxide ceramic films and membranes and, more specifically, to doping with chelated metals for enhanced fluorescence.

2. Description of the Related Art

As one of the dominant sensing technologies, and due to its high sensitivity and multiplexing capability, fluorescence detection have been widely used for different applications such as medical imaging, biological detection, in vitro diagnostics, and DNA sequencing. In order to further improve its sensitivity, a variety of advanced fluorescence substrates, including metallic nanostructure substrates and some semiconducting or metallic oxide nanostructure substrates, have been developed in the past decades. The physical mechanism for the metal-enhanced fluorescence (MEF) is due to the interactions of the excited fluorophores with surface Plasmon resonances in metal nanoparticles. However, the metals involved are usually expensive noble metals such as Au or Ag or toxic such as Cd and Se. In addition, the fluorophores have to be separated from the surface of the metallic nano-particles by a thin layer (i.e., tens of nanometers) of a dielectric material in order to avoid the fluorescence quenching effect, resulting in some complicated experimental procedures. Very recently, there has been a renewed interest toward europium complexes carrying electron-donating functionalized such as pyridines and picolinic acids.

In contrast, for fluorescence enhancement with non-metallic nanomaterials such as anodized aluminum oxide films (AAO) and anodized aluminum membranes (AOM), a layer of dielectric material is not required. In fact, the largest fluorescence enhancement can be achieved when the fluorophores are directly placed on the surfaces of these oxide films. One additional advantage of utilizing aluminum oxide ceramics for fluorescence enhancement is their electron-donating capabilities, a highly utilized effect in heterogenous catalytic processes with noble and rare-earth metals.

The first processes for producing aluminum oxide films using electrochemical anodization employed aluminum as an anode in an electrochemical cell and an acid solution (typically oxalic, sulfuric, phosphoric, etc.) an electrolyte. Under most conditions, an amorphous oxide layer is produced. A two-step anodization method was developed to produce ordered (hexagonal close pack) porous aluminum oxide, based on the observation that for a specific acid concentration, temperature and biased voltage, the first anodization is capable of producing ordered pores over time. Recent advances in the synthesis of nano-structured aluminum oxide films have made it possible to precisely control the morphology as well as physical and chemical properties of anodic aluminum oxide films (close pore) and membranes (through open pores). For example, synthetic nano-structured materials have been produced without the use of cytotoxic chemicals such as mercury and chromium. These materials have important biological and medical applications that involve sorting, sensing, isolating, and releasing biological molecules, an extremely attractive material for healthcare and biotechnology applications. However, there remains a need for nano-structured ceramic films and membranes yielding controlled levels of fluorescence enhancement at desired wavelengths, for specific fluorophores, with minimum unwanted auto-fluorescence that can interfere with the fluorescence reading and with non-cytotoxic manufacturing processes that can accomplished in safer and less expensive working environment, eliminating materials that are expensive to ship, handle or dispose of.

BRIEF SUMMARY OF THE INVENTION

The present invention comprises nano-structured ceramic films and membranes yielding controlled levels of fluorescence enhancement. The present invention further comprises a method of producing such films and members by doping during the film syntheses process. The present invention thus provides a material with controlled fluorescence enhancement properties and also creates a safer working environment that significantly reduces costs by eliminating cytotoxic materials that are expensive to ship, handle or dispose of. The method of the present invention provides a systematic set of steps for the production of doped controlled nano-structured aluminum oxide ceramic films—with random, ordered, closed or open pores—using fewer steps than traditional production methods and resulting in predictable levels of fluorescence enhancements at specific wavelengths (dependent upon choice of dopant). The present invention thus provides a high quality finished biocompatible product suitable for health and biotechnology bio-assay, biosensing and sequencing applications.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of a doped aluminum oxide construct according to the present invention;

FIG. 2 is a structural diagram of a bi-dentate, oxalate ligand, chelated metal center for doping nano-structured aluminum oxide for enhanced fluorescence through Forster resonance energy transfer (FRET). Actual FRET centers may have from one two three oxalate anions once incorporated into the ceramic film but must have a negative charge in solution prior to incorporation. FRET centers are a metal, metalloid, lanthanide, or actinide species in their various oxidation states;

Figure 7:
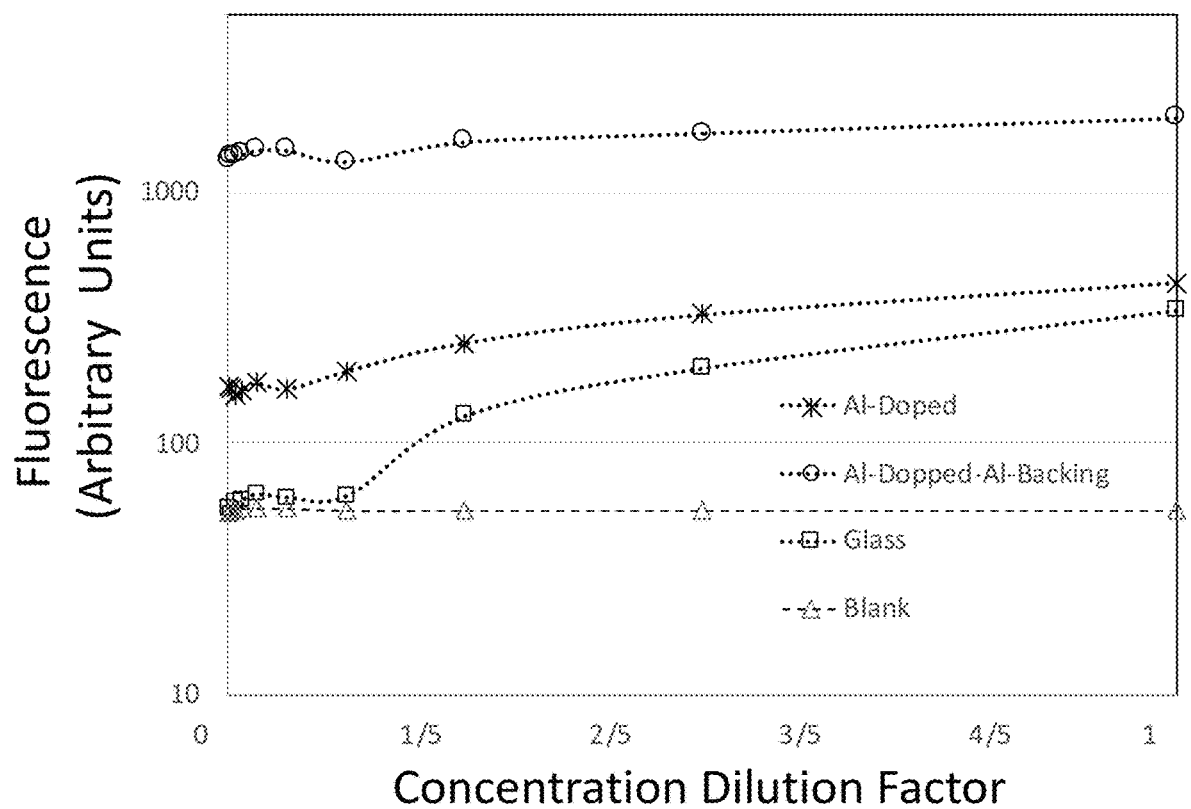
Figure 8:
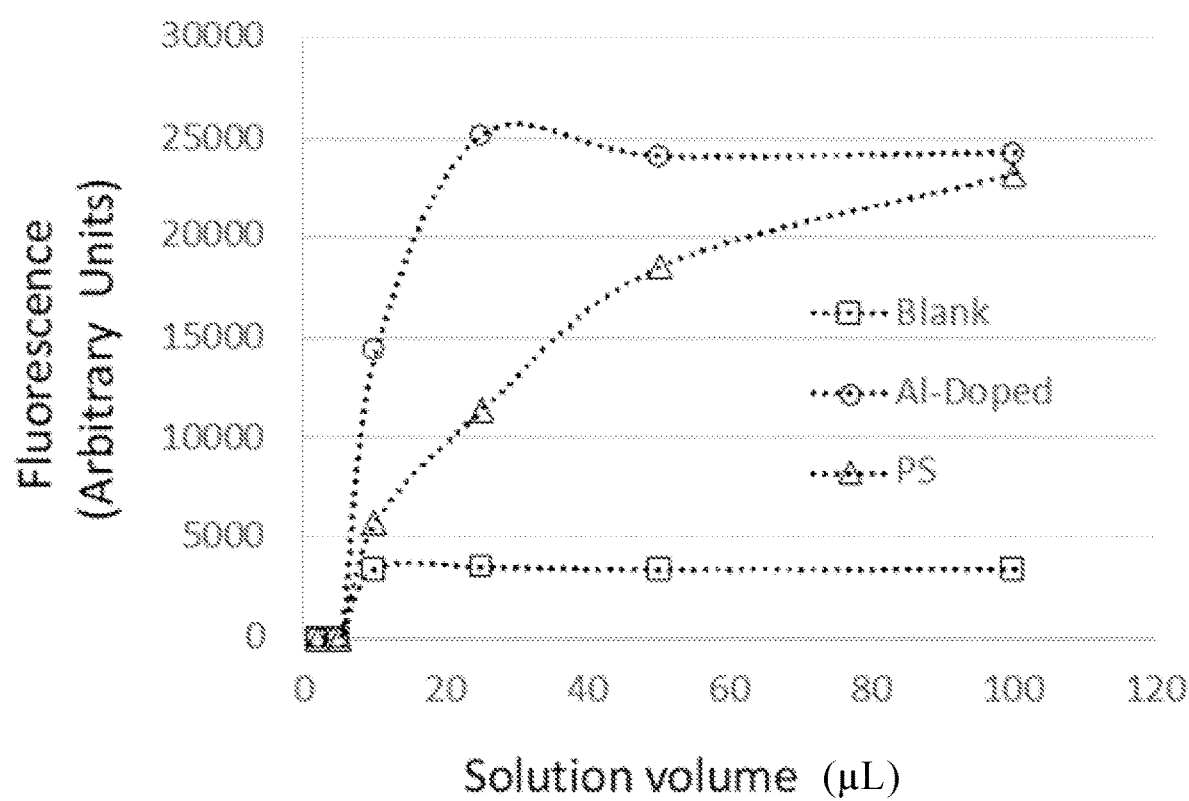
Figure 9:
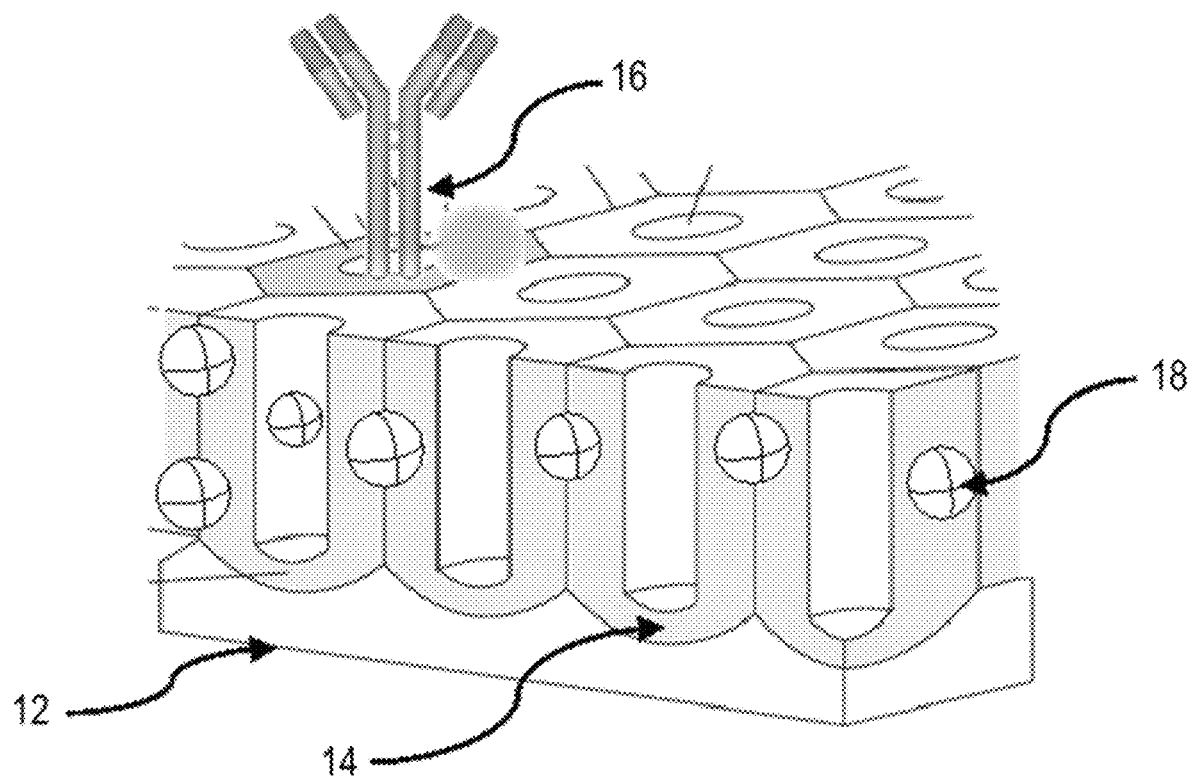
Figure 10:
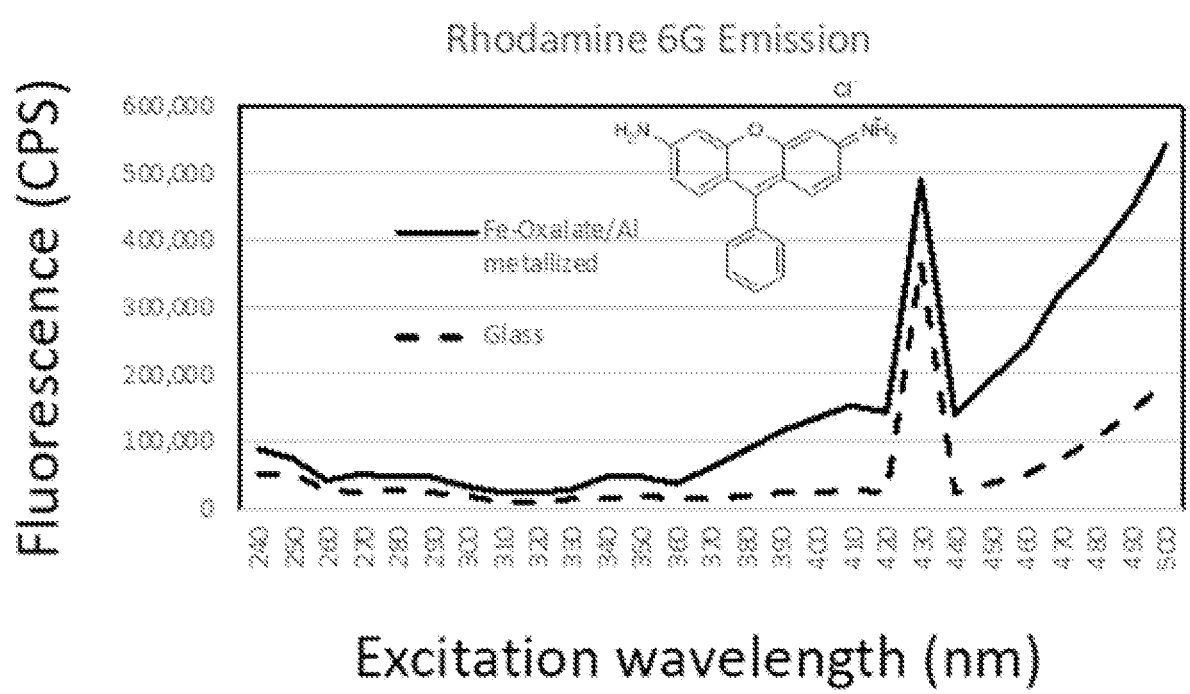

FIG. 7 is a graph of fluorescence results (vertical logarithmic scale) for Al-Doped, Al-Doped with aluminum metal backing, glass with fluorophore, glass with buffer no fluorophore (blank), where the fluorophore is goat poly clonal antibody to mouse, AlexaFluor 488 and the dilution factors from 1 to ½ to ⅟₅₁₂ of the original solution prepared as 1:1000 of the commercially available concentration (2 μg/ml);

FIG. 8 is a graph of fluorescence (arbitrary units) measured on a 96 well PS (polystyrene) flat bottom microplate as a function of sample size (micro-liters) where the fluorophore is Alamar Blue at constant 1:1000 concentration;

FIG. 9 is a schematic of a doped metallized nano-structured ceramic film according to the present invention;

FIG. 10 is a graph of the Rhodamine 6G emission spectra for glass and iron oxalate doped nano-structured ceramic film, where the test volume is 50 μL.

Figure 11:
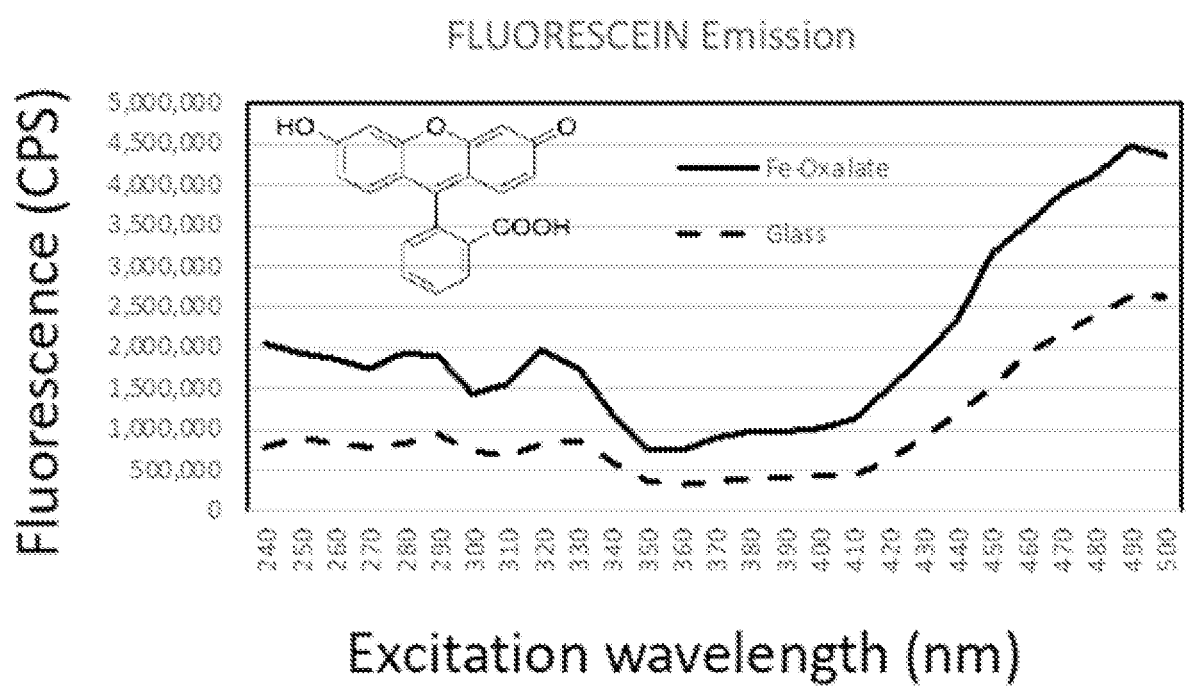

FIG. 11 is a graph of the fluorescence emission spectra for Fluorescein on glass and iron oxalate doped nano-structured ceramic film, where the test volume is 50 μL.

Figure 12:
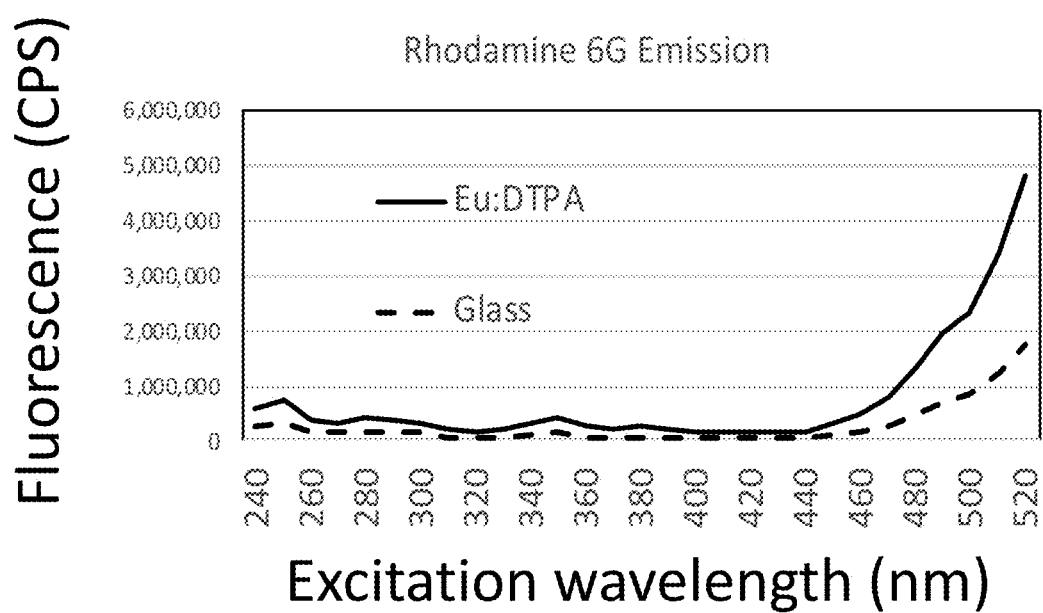

FIG. 12 is a graph of the Rhodamine 6G emission spectra for glass and iron oxalate doped nano-structured ceramic film, where the test volume is 50 μL.

Figure 13:
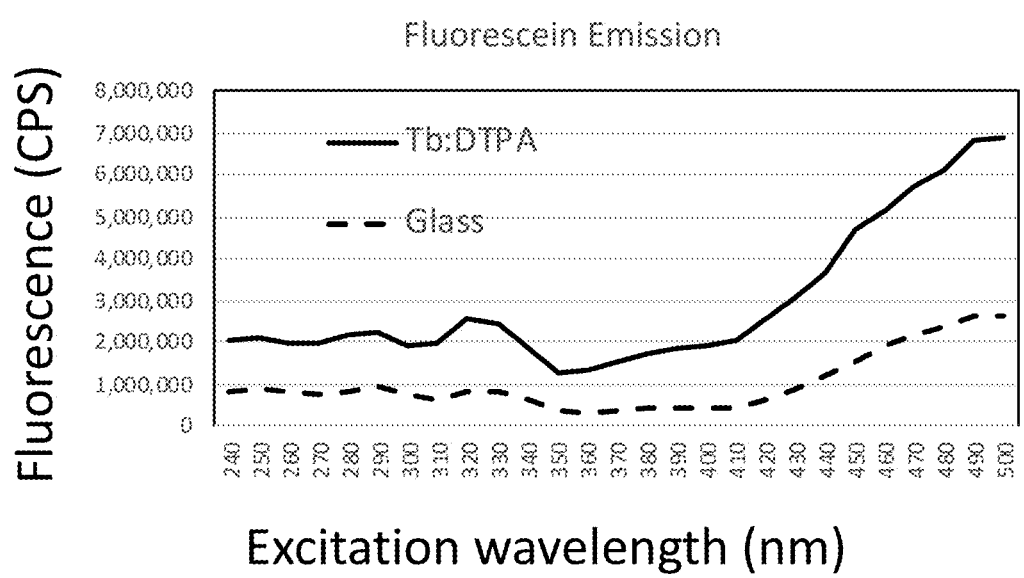

FIG. 13 is a graph of the fluorescence emission spectra for Fluorescein on glass and Terbium [Tb:DTPA] doped nano-structured ceramic metallized film, where the test volume is 50 μL.

DETAILED DESCRIPTION OF THE INVENTION

Figure 1:
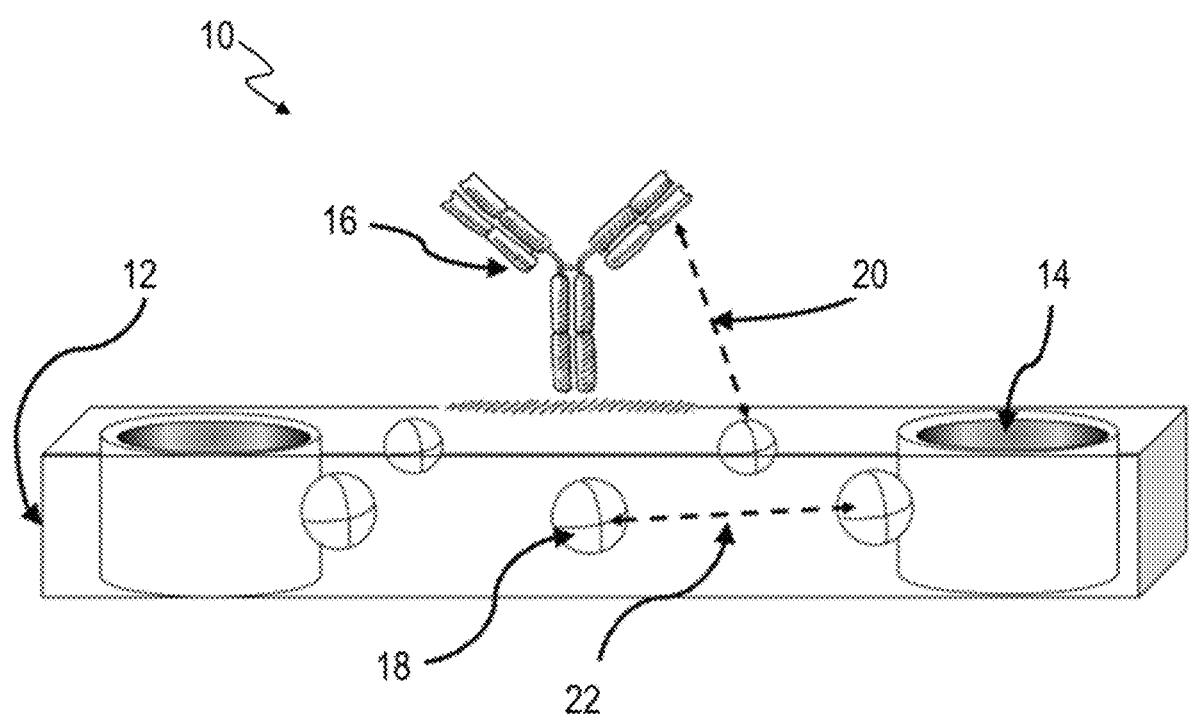
Figure 2:
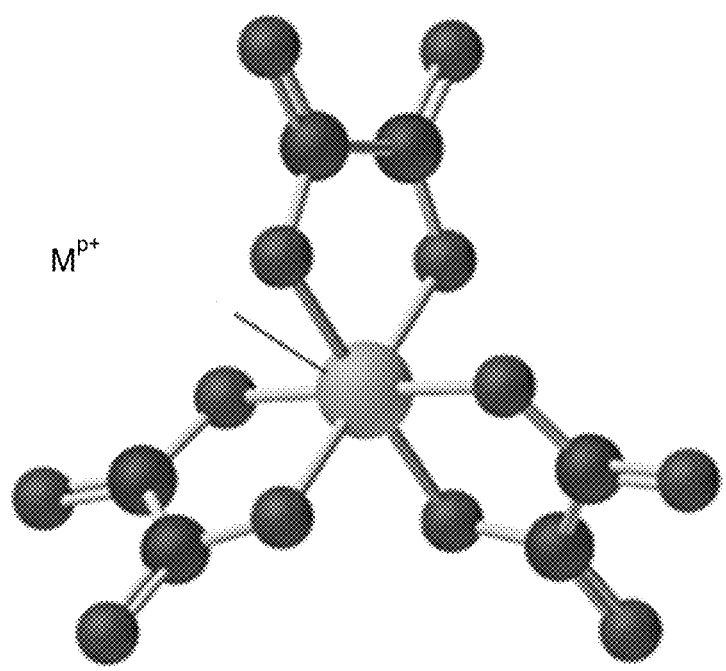
Figure 3:
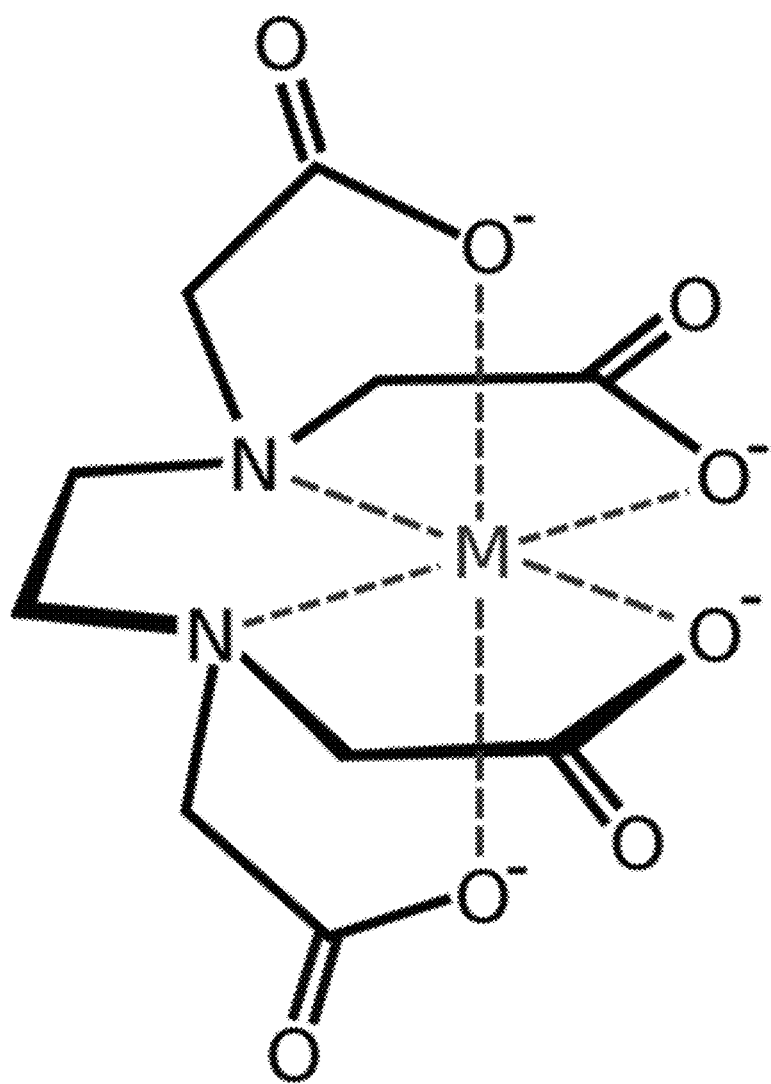
FIG. 3 is a structural diagram of an exemplary multi-dentate, EDTA ligand, chelated FRET center. In this specific case, any oxidation state for the metal with charge q<+4 yields a suitable anion for doping.

Referring to the figures, wherein like numeral refer to like parts throughout, there in seen in FIG. 1 a doped nano-structured aluminum oxide construct 10 according to the present invention. Construct 10 comprises an aluminum oxide substrate 12, a plurality of ceramic film nano-pores 14, a fluorescent tagged antibody or other suitable biological such as an antigen, oligonucleotide, fusion protein (acceptor) 16, a doping FRET center 18 comprising chelated metal ions (fluorescence donor) embedded in aluminum oxide substrate 12. The inter-distance between FRET units and antibody 20 is identified, and well as the controlled inter-distance 22 between FRET centers 18. Construct 10 may comprise a doped nano-structured aluminum oxide film or a doped nano-structured aluminum oxide membrane. As explained below, the present invention also comprises a method of making the doped nano-structured aluminum oxide film or membrane that avoid the use of materials that are costly due to their hazardous nature.

The method of the present invention is able to fabricate a nano-structured aluminum oxide film in which fluorescence enhancement doping centers are not simply contained within the open spaces of the ceramic film nano-pores but are embedded into the aluminum ceramic film to avoid leaching into the environment. Furthermore the chelated FRET center metal is isolated from the quenching effects of water. This result is achieved by means of a chelating anion used to form a doped chelant solution, which is added to the anodizing solution during the process of forming a ceramic film from high purity aluminum foil or plate. The doped ceramic film may contain FRET fluorescence enhancement doping centers (M) and chelating anions (A), such as oxalate, sulfate, cyanate, phosphate, bicarbonate and/or mono and multi-dentate organic ligands, to have the formula $$M^{+p}(A^{-n})_m$$

where M is a metal, a metalloid, a lanthanoid or an actinoid element in any of their oxidation states m that obeys the rule:

$$n*m > p$$

The method of the present invention is able to fabricate a nano-structured aluminum oxide film in which fluorescence enhancement doping centers are not simply contained within the open spaces of the ceramic film nano-pores but are embedded into the aluminum ceramic film to avoid leaching into the environment. Furthermore the chelated FRET center metal is isolated from the quenching effects of water. This result is achieved by means of a chelating anion used to form a doped chelant solution, which is added to the anodizing solution during the process of forming a ceramic film from high purity aluminum foil or plate. The doped ceramic film may contain FRET fluorescence enhancement doping centers (M) and chelating anions (A), such as oxalate, sulfate, cyanate, phosphate, bicarbonate and/or mono and multi-dentate organic ligands, to have the formula $$M^{+p}(A^{-n})_m$$

where M is a metal, a metalloid, a lanthanoid or an actinoid element in any of their oxidation states m that obeys the rule:

$$n*m > p.$$

Optionally NaF and KF salts can be added as the source of alkali ion because fluoride ions bind to the free coordination site of the donor M and help keep away water molecules, which cause quenching of donor luminescence.

The present invention thus provides a method to manufacture controlled doping of high purity nano-porous aluminum oxide membranes suitable for fluorescence enhancement. Importantly, the process does not require the use of highly cytotoxic metals (Cr, Cu, Hg) or organic solvents or perchloric acid. The present invention also does not produce toxic waste products.

Doped ceramic films according to the present invention may be used in assays involving fluorescence methods such as Forster resonance energy transfer (TR-FRET), Fluorescence-lifetime imaging microscopy (FLIM), Fluorescence polarization immunoassay (FPIA), Fluorescence anisotropy or fluorescence polarization, Fluorescence recovery after photobleaching (FRAP), Fluorescence Loss in Photobleaching (FLIP), Fluorescence correlation spectroscopy (FCS), and Falck-Hillarp fluorescence (F-H). Doped ceramic films according to the present invention may be used for the healthcare and biotechnology industry to in vitro diagnostics, ELISA bio-assays, immunohistochemistry assays, cell sorting, DNA and RNA sequencing, biosensing, high throughput drug discovery, secondary antibody R&D and fluorophore discovery.

The present invention encompasses the use of organic molecules, including oxalate ($C_2O_4^{-2}$) anions, and transition metals that form strongly absorbing chelants. The transition metals and organic chelants are embedded into a ceramic film or membrane during the electrochemical synthesis steps, neither by immersion of finished films and membranes nor by ion implantation. Table 1 below provides examples of chelating agents with various metals oxidation states which act as dopants in AAO films and membranes for FRET fluorescence enhancement, i.e., ethylenediaminetetraacetic acid (EDTA), L-glutamic acid, N,N-diacetic acid (GLDA), trisodium dicarboxymethyl alaninate (MGDA), hydroxyethyliminodiacetic acid (EDG), diethylenetriaminepentaacetic acid (DTPA), ethylenediamine N—N'—N' triacetic acid (HEDT). Numbers indicate the stability constants Log K values. The depicted compounds are merely intended to illustrate a class of groups and is not intended to, and does not limit, the present invention to such compounds.

TABLE 1

Exemplary chelating agents with various metals oxidation states

| Metal ion | EDTA | GLDA | MGDA | EDG | DTPA | HEDTA |
|---|---|---|---|---|---|---|
| Al3+ | 16.4 | 12.2* | 7.7 | 18.6 | 14.4 | |
| Ba2+ | 7.9 | 3.5 | 4.8 | 3.4 | 8.7 | 6.2 |
| Ca2+ | 10.6** | 6.4** | 7.0 | 4.7 | 10.8 | 8.1 |
| Cd2+ | 16.5 | 9.1* | 10.6 | 7.4 | 19.0 | 13.7 |
| Co2+ | 16.5 | 10.0* | 11.1 | 8.0 | 18.8 | 14.5 |
| Cu2+ | 18.8 | 13.1 | 13.9 | 11.8 | 21.2 | 17.4 |
| Fe2+ | 14.3 | 8.7* | 8.1 | 6.8 | 16.2 | 12.2 |
| Fe3+ | 25.1 | 11.7* | 16.5 | 11.6 | 28.0 | 19.7 |
| Hg2+ | 21.5 | 14.3 | 5.5 | 26.4 | 20.1 | |
| Mg2+ | 8.7** | 5.5** | 5.8 | 3.4 | 9.3 | 7.0 |
| Mn2+ | 13.9 | 7.6* | 8.4 | 5.5 | 15.2 | 11.1 |
| Ni2+ | 18.4 | 10.9* | 12.0 | 9.3 | 20.1 | 17.1 |
| Pb2+ | 18.0 | 10.5* | 12.1 | 9.4 | 18.8 | 15.6 |
| Sr2+ | 8.7 | 4.1 | 5.2 | 3.8 | 9.8 | 6.8 |
| Zn2+ | 16.5 | 10.0* | 11.0 | 8.4 | 18.2 | 14.6 |

Lanthanide elements such as Europium and Terbium in various oxidation states (+2, +3, +4) have been found especially useful for FRET applications. Time-resolved fluorescence resonance energy transfer (TR-FRET) assays are homogeneous proximity assays in which energy is transferred from a donor to an acceptor molecule. A number of TR-FRET platforms are currently available that differ principally in the nature of the donor and acceptor dyes.

An embodiment of the present invention uses an Europium chelate (Eu) as donor dye, which offers a number of advantages, including a high quantum yield, large Stokes' shift and a narrow-banded emission at around 615 nm. Furthermore, the lifetime of emitted light from Eu chelate dyes is exceptionally long, allowing for time-delayed measurements. The unique fluorescence properties of Eu chelates make them ideal energy donors in TR-FRET assays. In prior art the Europium chelates are covalently attached to antibodies to form FRET pairs with secondary (fluorophore tagged) antibodies. Fluorescence occurs only when both FRET pairs are in close proximity (~Ro) to each other. If both antibodies are specific to the same antigen it can be used as an ELISA bio-assay without the need for fixation, incubation, and multiple washes. In the present invention, Europium is deeply deposited during manufacturing inside the ceramic films to prevent from leaching into bio-assay solutions. Because Europium is not covalently linked to an antibody, the present invention has a more general use then FRET pairs used in solution. For example, any antigen can be bound to the surface of the ceramic film where it will be recognized by a tagged antibody obviating the need for a primary FRET tagged antibody altogether. The present invention shares the same advantages of solution based FRET pairs, but without requiring two antigen specific antibodies. This makes the present invention more general and of wider applicability.

In order to successfully incorporate the FRET centeres into anodic oxides, the incorporated ions should be stable in the electrolyte and neutral or negatively charged through the use of a chelant anion. Anodic aluminum oxide may be successfully doped and, by way of doping, impart new properties to the anodic oxide.

Figure 4A:
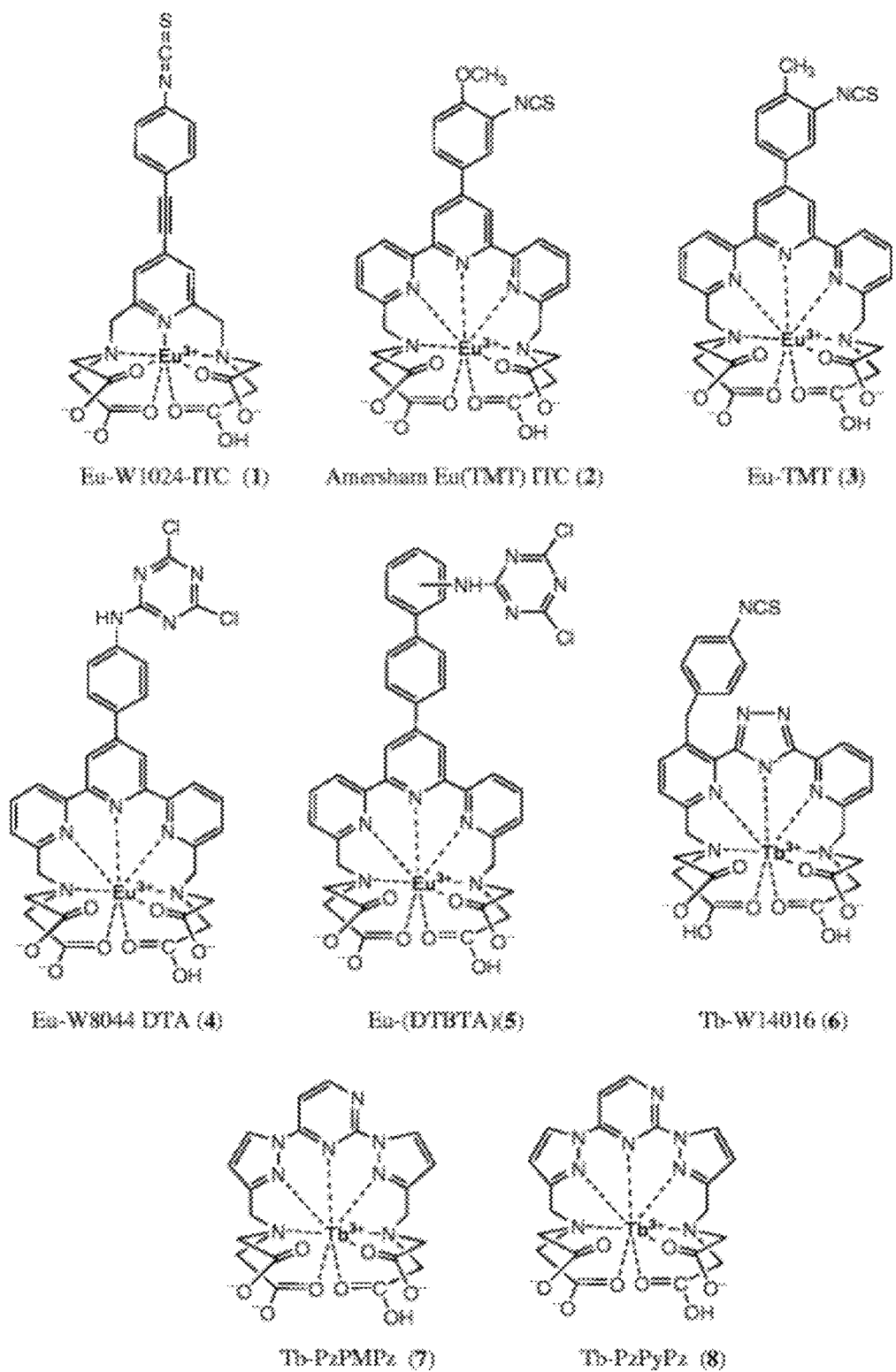
FIG. 4 is a series of structural diagrams of various aromatic organic ligands commonly used for forming FRET pairs for biological sensing applications.

The method of the present invention achieves effective incorporation of chelated metals in anodic aluminum oxide. Chelates leading to electrically neutral species, such as EDTA, are shown in FIG. 4. The aromatic ligand groups serve as an antenna for energy transfer to the lanthanide centers as well as shields it from water coordination. For Terbium$^{+4}$, the EDTA chelate, although stable in solution, is neutral and thus has low mobility towards the anode. Tb(EDTA) is not a good doping species.

In the present invention positive ions, such as $Eu^{+2}$, $Eu^{+3}$, all lanthanides, actinides and other metals as shown in Table 1, are prepared with excess negatively charged chelates. Such is the case of EDTA with any $M^{+3}$ ionic species. For oxalate chelates, the general formula:

$$M^{+p}(C_2O_4^{-2})_m$$

with the rule $$2m > p$$

yields soluble species with high mobility. In general, any chelated species with formula:

$$M^{+p}(A^{-n})_m$$

that obeys the rule:

$$n*m > p$$

is capable of yielding soluble anionic species with high mobility during anodization and satisfactory incorporation into aluminum oxide films.

As an example, for a metal with a common +3 oxidation state, such as $Eu^{+3}$, oxalate chelates with m=2, 3 lead to anion species suitable for incorporation into anodic aluminum oxide.

Since anodizations are typically carried out at low pH, there is an equilibrium of anions depending on the exact pH of the solution. Europium oxalate is highly insoluble both in di-ionized water as well as in a saturated oxalic acid solution. Thus, one has to account for the solubility of the metal:chelant pair in the anodizing solution (e.g., 0.3 M oxalic, sulfuric or phosphoric acid). For instance, Europium oxalate $Eu_2(C_2O_4)_3$ is highly insoluble in water as well as in a saturated oxalic acid solution.

A doped nano-structured aluminum oxide film or membrane suitable for enhanced fluorescence is fabricated using solutions metals in various oxidation states. The method of the present invention generally comprises the steps of doping solution preparation and nano-structured aluminum oxide film preparation. FRET efficiency, fluorescence enhancement may then be determined or confirmed.

Figure 5A:
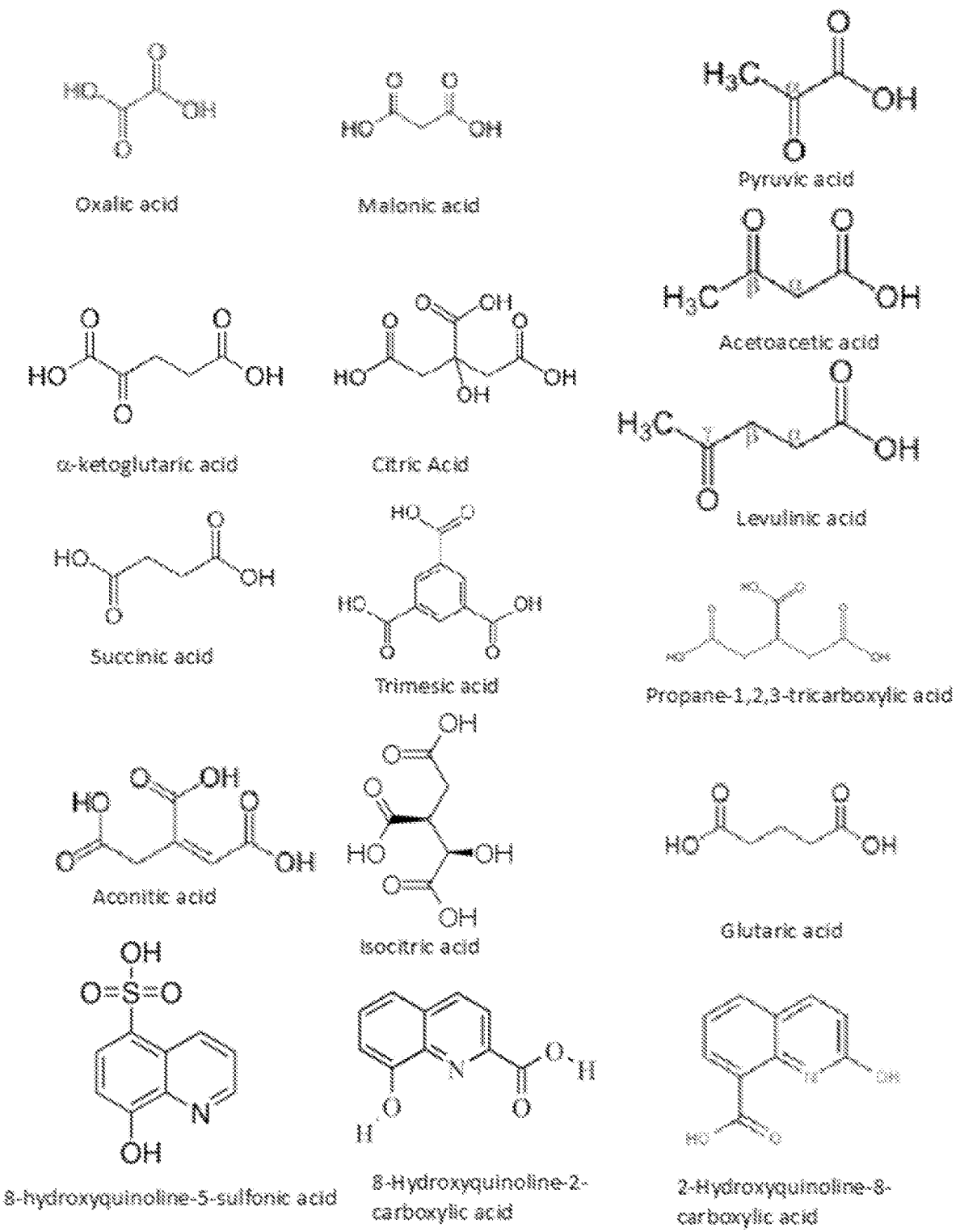
FIGS. 5A and 5B are a series of structural diagrams of open chain and macrocyclic polyminopolycarboxylic acids, carboxylic derivatized crown ethers, polycarboxylic and polyphosphonic acids suitable for doping FRET centers into a nano-structured ceramic film during manufacturing from an anodizing solution.
Figure 5B:
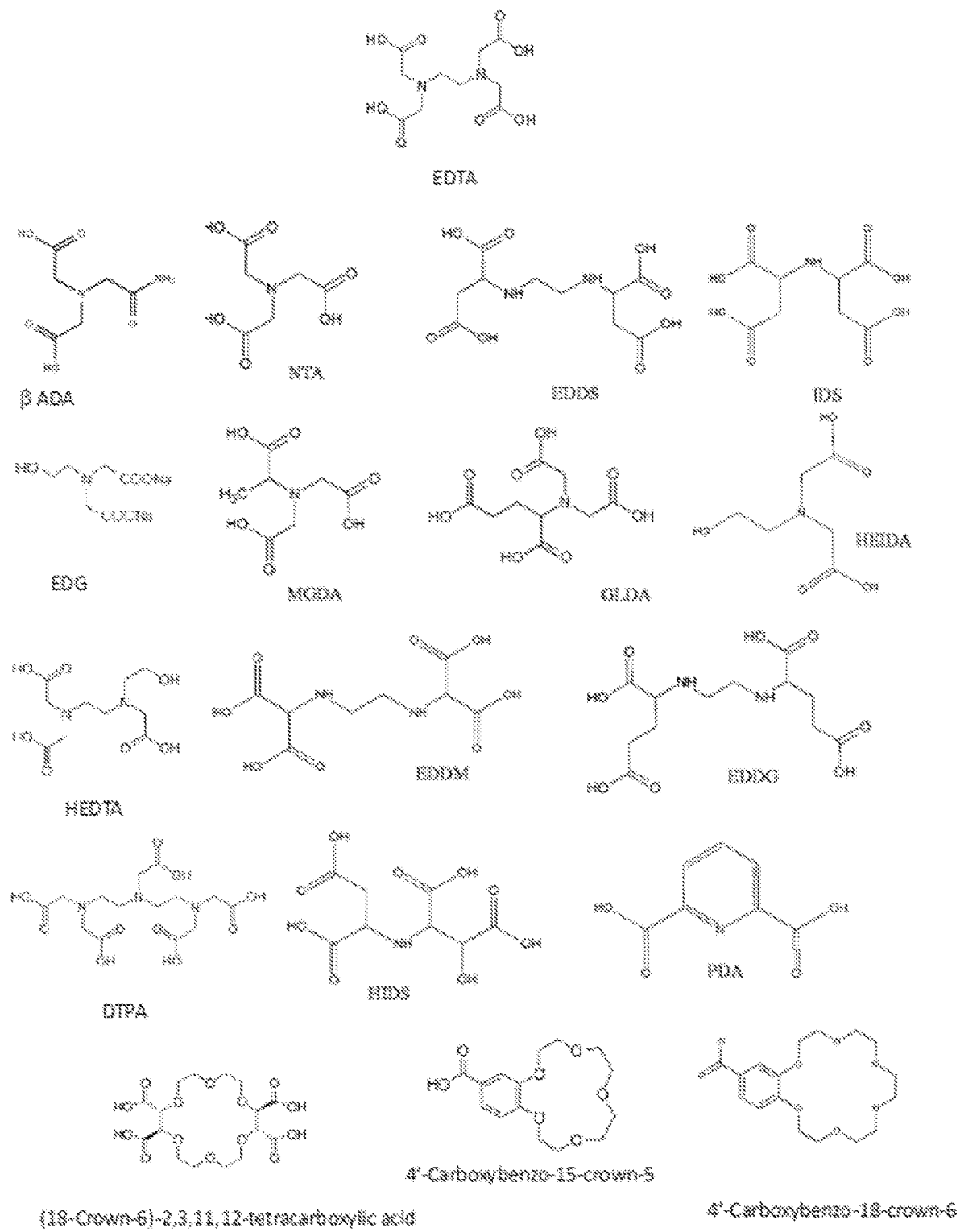
Figure 6:
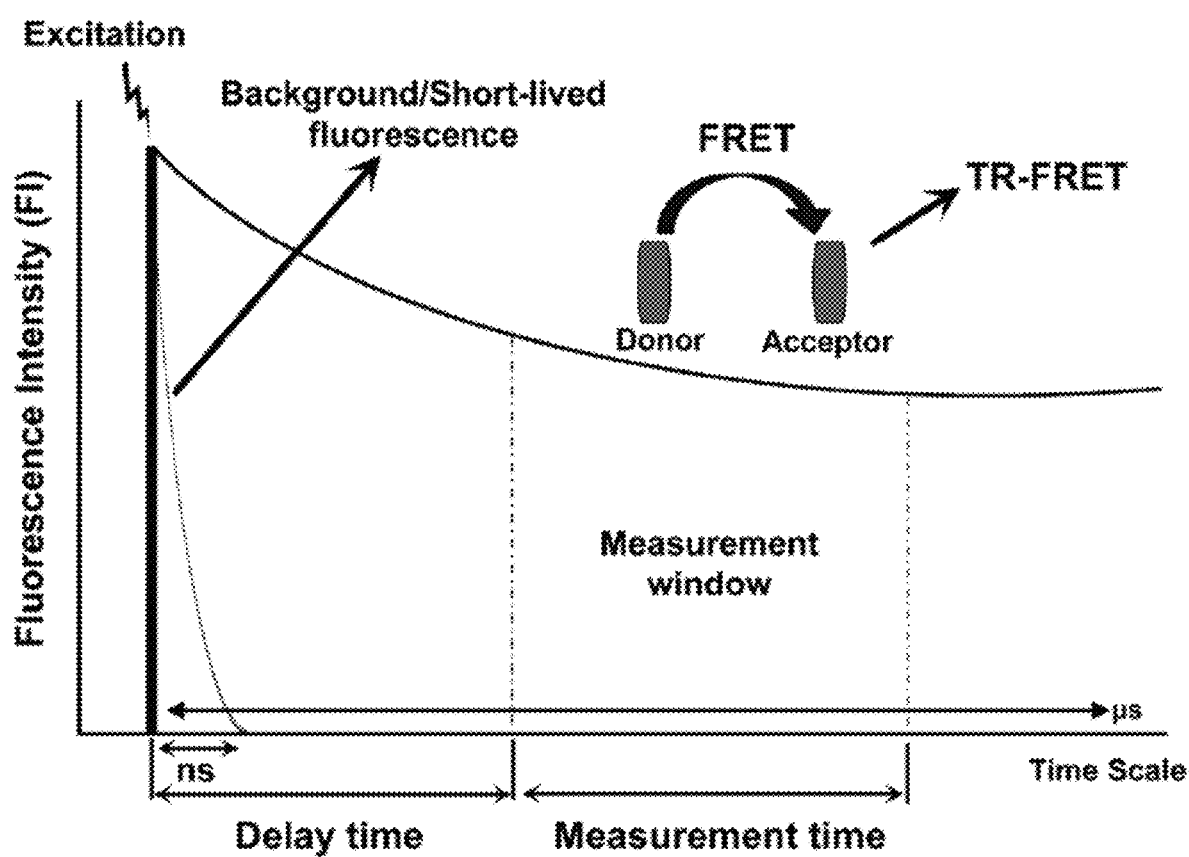
FIG. 6 is a graph of Time Resolved Fluorescence Resonance Energy Transfer (TR-FRET) showing that a time delay, on the order of a few hundred nano-seconds, eliminates short-lived (nano-second) fluorescence from unbound fluorophore in solution, the quenched ceramic film background (auto-fluorescence) and fluorescence from other compounds present in solution.

The preparation of a doping solution involves the direct doping of pure aluminum with lanthanides and actinides prior to anodization and is straightforward. To prepare a soluble $M^{+p}(C_2O_4^{-2})_m$ doping solution, with (2m>p), one must begin with fresh solutions of two or more soluble species. For example, to prepare a doping solution of Europium III (Eu+3), one may start with a chloride salt, $EuCl_3$, and potassium or sodium hydroxide. All of these salts are highly water soluble. First, a solution of a $EuCl_3$ at concentrations C between 0.01M to 0.1 mM is prepared at room temperature. Next, a potassium or sodium hydroxide solution of concentration 3C is prepared and heated to approximately 50° C. with magnetic stirring. Solution 1 is poured slowly to obtain the hydroxide $Eu(OH)_3$. Most lanthanide and actinide hydroxides are insoluble in water. Next, the solution is centrifuged and the yield determined by weighing the residual solid after oven drying overnight at 100° C. Next, a chelating solution is prepared with solution 3 which consists of adding an equimolar amount of one of the acid compounds in FIG. 4 and FIG. 5, including oxalic acid. For crown ethers, as seen in FIG. 5, it is advantageous to derivatize with carboxylic functionality to add negatively charged species, such as carboxylate anions, for a more effective incorporation into the ceramic film during anodization. The acid is added to solution 3 under constant stirring until the solution appears clear. The final pH is adjusted to a range between pH=8 to pH=10. This is referred to as the doping mixture solution. Finally, Add sufficient volume of the doping mixture to the anodizing solution to yield a doping concentration >$5.0 \times 10^{-3}$ M. This solution is referred to as the "doped chelant solution."

The preparation of a nano-structured aluminum oxide film involves the use of the above prepared solution together with the following procedure to prepare nano-structured aluminum oxide films with fluorescence enhancement properties. First, a high purity (>99.99%) aluminum plate is degreased and then electro-polished. This pre-anodizing plate is then placed in a mixture of anodizing and the doped chelant solution discussed above for 10-20 min. The plate is then lifted 1 cm out of the mixture solution to avoid corrosion at the air interface and anodization continued to achieve desired aluminum oxide thickness. The desired format is cut from the anodized place (double sided anodization with a remaining aluminum core) or the anodized plate is subjected to membrane separation. Membrane separation involves the creation of a soluble membrane for separation or the use of pulse voltage membrane delamination. The cutting and membrane separation may be repeated until the plate thickness is comparable to thickness of a detached anodized oxide layer. The plate is then anodized a final time without detachment to generate an aluminum-backed nano-structured ceramic film highly suitable for fluorescence enhancement.

FRET Efficiency and fluorescence enhancement determination may be accomplished by cleaning the films in peroxide solution and oven drying for 2 hours. Alternatively, the films can be annealed at no more than 500-550° C. to further clean and increase enhanced fluorescence effects. FRET efficiencies may then determined by directly measuring fluorescence ratios compared to a standard substrate such as glass.

Examples of fluorescence enhancement results obtained with such doped ceramic films, including doping by transition and post-transition metals and lanthanides are presented below:

Example 1

FIG. 7 shows fluorescence results (vertical logarithmic scale) for fluorophore on a) Al-doped nano-structured ceramic film, b) Al-doped/Al-backed (aluminum metal backing), c) glass flat bottom with fluorophore, and d) glass with buffer only without fluorophore (blank). Fluorophore is goat polyclonal antibody to mouse, a tagged goat antibody, IgG H&L, distributed by Abcam a manufacturer of research antibodies, kits and assays for biological research, as ab150113. Host species goat. Target species mouse. The antibody, AlexaFluor 488, has been tested for suitability in the bio-assays ICC/IF, ELISA, Flow Cyt, IHC-P successfully. Excitation wavelength: 495 nm. Emission wavelength: 519 nm.

A mother fluorophore solution was prepared as 1:1000 of the purchased concentration (2 µg/ml). Dilution factors from 1/2 to 1/512 from the mother solution were then deposited in triplicate on a flat glass bottom, 96 well micro-plate, and values read with a BioTek Synergy 2 microplate reader after 5 minutes to allow penetration into the nano-structured film. Table 2 below presents the raw data for this example.

TABLE 2

Typical FRET enhancement values obtained with the present invention using Aluminum doping in through pore membranes and in Aluminum backed films. Refer to the main text for experimental details.

| Concentration | Al-Doped | Al-Doped-Al-Backing |
|---|---|---|
| 1 | 123% | 583% |
| 1/2 | 156% | 858% |
| 1/4 | 186% | 1221% |
| 1/8 | 299% | 2116% |
| 1/16 | 258% | 2385% |
| 1/32 | 263% | 2316% |
| 1/64 | 259% | 2338% |
| 1/128 | 255% | 2393% |
| 1/256 | 304% | 2675% |
| 1/512 | 295% | 2409% |
| average | 240% | 1929% |

The average enhancements are between 240% for Al-doped and 1900% for Al-doped/Aluminum backed films. Note that the actual enhancement is higher for higher dilutions of the fluorophore. This is direct indication that the process is FRET induced. As the dilution increases the solution above the substrate (ceramic or glass) becomes more transparent and the total fluorescence is due mostly to the fluorophore directly in contact (to within 10 nm) with the ceramic film.

Example 2

FIG. 8 shows fluorescence results for an Al-doped nano-structured ceramic film and flat bottom (polystyrene) with Alamar Blue fluorophore at various volumes but constant concentration (1:1000). The blank sample contains buffer only without fluorophore (blank). All measurements were carried out in triplicate as bottom reads with 50% sensitivity setting on a PS flat bottom 96 well micro-plate BioTek Synergy 2 reader. Recommended bio-assay tests require 100 micro-liters of solution. For a 6.4 mm disc (typical of a 96 well microplate) the ceramic film requires only 10 micro-liters to cover and saturate the nano-structured ceramic. Constant fluorescence between 20-100 micro-liters for the doped nano-structured film is indicative that most of the fluorescence is coming from the enhanced contact volume, a direct indication the FRET is at work. Over 50% of the total fluorescence is due to this small volume in the Al-doped film. For the PS flat bottom wells the amount of fluorescence decreases significantly within this volume range. Enhancement factors vary between 100% for 100 µL to 600% for 10 µL samples. This indicates that doped ceramic films can significantly reduce the use of expensive reagents while simultaneously increasing bio-assay sensitivity, somewhat counter-intuitive but relatively simple to explain through the FRET mechanism. Only the volume in close proximity to the ceramic film is fluorescence enhanced.

Example 3

FIG. 9 shows an example of a doped nano-structured ceramic with the aluminum backing left in place. Using a transition metal, such as Fe, iron as a nano-structured ceramic film containing iron oxalate, $Fe_2(C_2O_4)_3$ as FRET centers was prepared at concentrations between 0.01 and 0.0005 M and place into the anodizing solution. Through pore (no aluminum backing) analogue were also prepared for comparison purposes, both with thickness between 50-100 microns.

Discs were cut from these films measuring 11 mm in diameter were prepared and placed in a horizontal powder holder (SC15) of an FS5 (Edinburgh Instruments) spectrofluorometer. Fifty (50) µL of fluorophore solution was placed on the disc and after 5 minutes excitation-emission spectral maps were taken between 200-700 nm of the discs with and without fluorophores. Two fluorophores at micromolar concentrations were added separately and the emission spectrum measured near the manufacturer recommended excitation wavelengths, 525 nm for Rhodamine 6G and 498 nm for Fluorescein and enhancement calculated at the maximum emission wavelengths of 547 nm and 517 nm respectively.

FIGS. 10 and 11 show the emission spectra for both types of iron oxalate doped ceramic films. The enhancement factors when compared to a similar sized glass (SCHOTT) discs are 382% for Rhodamine 6G on doped $Fe_2(C_2O_4)_3$ metallized ceramic film and 165% for Fluorescein on non-metallized, through pore, doped $Fe_2(C_2O_4)_3$ ceramic films.

Example 4

Lanthanides such as Europium and Terbium FRET centers have been successfully integrated into time resolved FRET (TR-FRET) immunoassays. A target specific antibody is either conjugated directly to or is captured by an antibody conjugated to a Europium or Terbium chelate. The chelate is used to protect the $Eu^{+3}$ or $Tb^{+3}$ ionic species from the quenching effects of water as well as serve as 'antenna' to increase the absorption cross section of the lanthanide. The advantages of such antibody lanthanide chelate conjugate is to avoid tedious and time-consuming multiple washings required in ELISA bio-assays. In addition, time lagged fluorescence can be employed to distinguished between antigen bound and non-bound fluorescent antibody. Here we use the nano-structured ceramic film to protect the FRET center from water as well as to immobilize it for enhancement purposes for ANY fluorescent based bio-assay.

[DTPA:La] chelants were prepared with concentrations between 0.01 and 0.0005 M by neutralizing the lanthanide (La=Eu, Tb) hydroxide ($Eu(OH)_3$ and $Tb(OH)_3$) in solution directly with the polyaminoacetic acid DTPA. The chelant was added to anodizing solutions and through pore and metallized nano-structured ceramic films were prepared with 50-100 micron thickness.

As explained previously, discs were cut from these films measuring 11 mm in diameter and placed in a horizontal powder holder (SC15) of an FS5 (Edinburgh Instruments) spectrofluorometer. Fifty (50) µL of fluorophore solution was placed on the disc and after 5 minutes excitation-emission spectral maps were taken between 200-700 nm of the discs with and without fluorophores. Rhodamine 6G (25 micro-molar) and Fluorescein (2.4 mili-molar) were employed and their enhancement calculated at the maximum emission wavelengths of 547 nm and 517 nm respectively.

FIGS. 12 and 13 show the emission spectra for lanthanide doped nano-structured ceramic films. The enhancement factors when compared to glass discs are 393% for Rhodamine 6G (25 micro-molar) on through pore ceramic film doped with [Eu:DTPA] and 252% for Fluorescein (2.4 mili-molar) on metallized ceramic films doped with [Tb:DTPA]. Higher fluorescence enhancements are obtained from Fluorescein solutions at micro-molar concentrations (not shown).

What is claimed is:

1. A nano-structured aluminum oxide construct, comprising:
   an aluminum oxide substrate;
   a nano-pore formed in the aluminum oxide substrate to define an open space within the aluminum oxide substrate;
   a chelate embedded in the aluminum oxide substrate so that the chelate is incorporated into the aluminum oxide substrate and not contained in the open space of the nano-pore, wherein the chelate is a lanthanide; and
   an antibody, an antigen, a nucleotide, an oligopeptide, a fusion protein, or a biological molecule or fluorescent tagged versions of the antibody, the antigen, the nucleotide, the oligopeptide, the fusion protein, or the biological molecule bound to the aluminum oxide substrate.

2. The nano-structured aluminum oxide construct of claim 1, wherein the construct comprises a film.

3. The nano-structured aluminum oxide construct of claim 1, wherein the construct comprises a membrane.

4. A method of forming a nano-structured aluminum oxide construct, comprising the steps of:
   preparing a doped chelant solution including a lanthanide;
   anodizing an aluminum plate in an anodizing solution that includes the doped chelant solution to form an aluminum oxide film having nanopores defining open spaces in the aluminum oxide film, wherein the lanthanide is embedded in the aluminum oxide film so that the lanthanide is incorporated into the aluminum oxide film and not contained in the open spaces of nanopores; and
   binding an antibody, an antigen, a nucleotide, an oligopeptide, a fusion protein, or a biological molecule or fluorescent tagged versions of the antibody, the antigen, the nucleotide, the oligopeptide, the fusion protein, or the biological molecule to the aluminum oxide film.

5. The method of claim 4, wherein the step of anodizing the aluminum plate comprises lifting the aluminum plate partially out of the anodizing solution.

6. The method of claim 4, further comprising a step of cutting a predetermined format from the aluminum plate after the step of anodizing the aluminum plate.

7. The method of claim 4, further comprising a step of separating a membrane from the anodized aluminum plate step of anodizing the aluminum plate.

8. The method of claim 4, further comprising the step of anodizing the aluminum plate without detachment to form an aluminum-backed nano-structured ceramic film.

9. The method of claim 4, wherein the step of preparing the doped chelant solution comprises a step of creating a doping solution having the lanthanide in an alkaline solution to precipitate a chelating ion in a form of hydroxide.

10. The method of claim 4, wherein the step of preparing the doped chelant solution comprises steps of neutralizing a hydroxide with an organic or inorganic acid to a form an alkaline solution having a pH between 8 and 10.

11. The method of claim 4, wherein the step of preparing the doped chelant solution comprises steps of adding the chelant solution to an anodizing solution to concentrations between 0.1 mM to 10 mM.

12. The method of claim 4, further comprising a step of cutting the anodized aluminum plate into a format that is capable of being used for fluorescence enhancement in a bioassay instrument.

* * * * *